June 9, 1936. W. L. ARMACOST Plant Pat. 180
ROSE
Filed Jan. 6, 1936
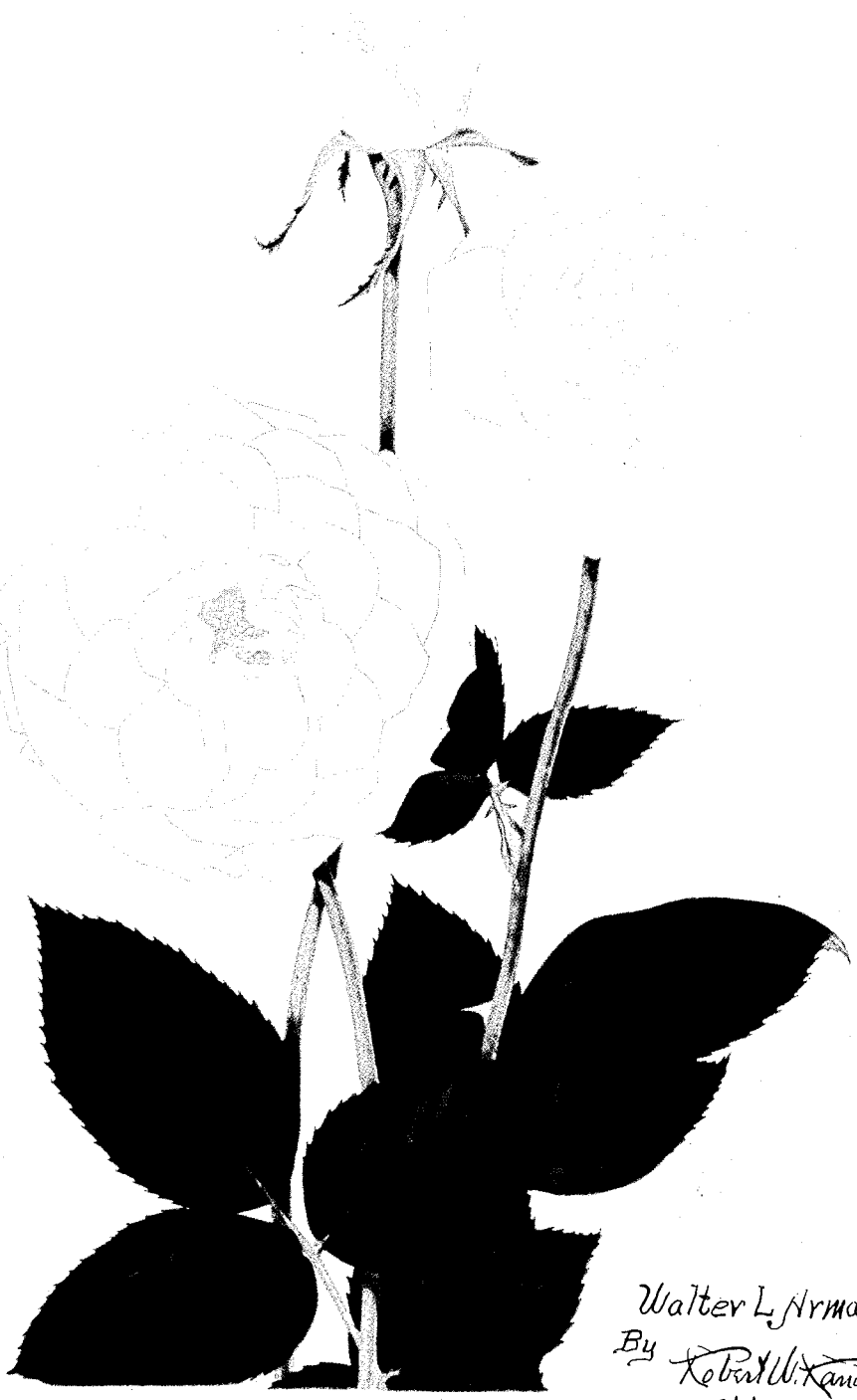
Walter L. Armacost;
By Robert W. Randle,
Attorney.

Patented June 9, 1936

Plant Pat. 180

UNITED STATES PATENT OFFICE

180

ROSE

Walter L. Armacost, Los Angeles, Calif., assignor to Armacost & Royston, Inc., Los Angeles, Calif., a corporation of California Application January 6, 1936, Serial No. 57,724

1 Claim. (Cl. 47—61)

This application relates to the discovery, development, and production of a new variety of rose, which was discovered in a green-house of Armacost & Royston, a corporation, located at No. 2003 Armacost Avenue, West Los Angeles, county of Los Angeles, State of California, where it originated as a sport from a rose-plant known by the trade name "Souvenir" (Plant Patent No. 25, issued August 30, 1932) in a green-house of said Armacost & Royston, Inc.

The grandparent of my new rose is known by the name of "Talisman".

The subject of this application was discovered by me in August, 1934, as a sport of said parent plant, after which I immediately took the proper steps to reproduce it, which I did asexually by budding, which about October 15th, 1934, produced a replica of the original sport above mentioned.

Said latter rose I immediately budded, and on January 1st, 1935, it also came true in every respect to its said parent. Said second product was then budded, and on February 15th, 1935, it also came true in every respect with relation to its parent, and to said sport.

Other roses, from the above, are now being propagated in the green-houses of said Armacost & Royston, Inc., which appear to be replicas of said sport and its said descendants.

In view of the above statements, I believe that the subject of this application is now permanently fixed as a new variety of rose.

*Class.*—The subject of this application is a new rose-plant which is classed as a hybrid tea yellow rose, which is very floriferous and presents a combination of colors, shades and tones which are especially attractive to the public and, as a tout-ensemble is considered as paramount to all other roses of its class.

*Illustration.*—Probably the best possible artificial example of my new rose is portrayed in the accompanying painting which forms a part of this description, the same being shown with the bloom in three states of development, viz: a bud beginning to open; a bloom approximately half open; and a fully matured bloom at its acme of natural artistry.

*Color standard.*—The references hereinafter mentioned as to colors, are designated by insignia which are found correspondingly in the book designated as "Robert Ridgway Color Standards and Color Nomenclature", published in the year 1912.

*Buds.*—The buds of my new rose are long, somewhat tapering and symmetrical. They are slightly longer than that of the rose Souvenir, above mentioned, and when grown under the same conditions, my rose is fuller, has a greater number of petals, the petalage being from forty to as many as sixty in number.

*Petals.*—Normally the outside face of the petals are "Lemon Chrome" (Plate IV) at the base, shading to "Cadmium Yellow" (Plate III), with a suffusion of "Flame Scarlet".

The inside surface of the petals present a rich-gold color with a suffusion of "Flame-Scarlet" (Plate II) in its early stage of development, turning to a deep "Cadmium Yellow" (Plate III) as the bloom expands and retaining the last mentioned color when the bloom is fully open, giving the mature bloom a rich, live golden effect.

*Bloom.*—The bloom of this rose measures at least four inches in diameter. The color of the central portion of each bloom, that is the corona, when the bloom is fully opened, presents a reddish-orange color, most nearly represented by "Spectrum Red", (Plate I), being darker than the corona of the rose "Souvenir", and of a more yellowish cast. The bloom of this rose measures, when fully open, at least four inches in diameter. This rose is free blooming and is what is known as recurrent continuous blooming.

*Sepals.*—Large and regular, wide at the base, and narrowing sharply to a point about two-thirds of the distance from the base and then widening out slightly toward the tip, thereby being lanceolate in shape. The tip is sharply pointed. The margin is entire, except for the serrate tip. The upper side is minimum green in color, and the under side is a grayish-green.

*Stamens.*—Arranged in regular order around the styles.

*Filaments.*—The filaments are of a reddish-orange color, otherwise they have no unusual features.

*Anthers.*—Yellow in color with a reddish-orange margin.

*Styles.*—Free from each other and are exserted about one-fourth of an inch above the mouth of the receptacle. They are pale yellow at the base and turn to bright pink at the apex.

*Stigmas.*—Nothing unusual, except that they are "Lemon Yellow" in color.

*Peduncles.*—Long and straight, normally vertical. Surface dark green and glabrous, very strong, and of ultra-vigorous growth.

Each peduncle is very long, stiff and erect, and of light greenish color, with its upper end merging into the hip by which the bloom is supported.

*Genitals.*—Have no particular features, as they are practically the same as that of the parent, and many other varieties of rose.

*Spines.*—Few in number, averaging three-eighths of an inch in length, and of light pink in color, with their points directed downwardly at an angle, and having a very strong base by which they are attached.

*Fragrance.*—This new rose has a rich, pronounced, continuous and pleasing tea-fragrance, which persists throughout the existence of the bloom.

*Disease.*—This rose is entirely resistant, has not had a suggestion of disease during its existence as a new rose.

*Transportation.*—Notably resistant to weather and other conditions, and after being cut it can be transported great distances without deterioration, therefore, it has been found to be especially adapted for shipment and mass-production.

*Cultivation.*—The production, development, and maintenance of this rose to an acme of perfection, was accomplished partly by careful propagation, combined with geoponic attention properly applied, and by reason of proper administration of natural elements mechanically applied, including air and temperature conditioning, combined with proper humidity applied thereto, all transpiring in the green-houses of said Armacost & Royston, Inc., at West Los Angeles, State of California.

Having now fully shown and described my new rose, what I claim and desire to secure by Letters Patent of the United States, is:

A new and distinct variety of rose, as herein described, characterized by its presentation of a very rich variegated warm orange coloration; the ability of the bloom to retain its beauty of coloration and shape to the point of its withering; its vigorous growth as a bush; its continuous blooming quality, and its pronounced continuous and pleasing tea fragrance throughout the existence of the bloom.

WALTER L. ARMACOST.